US006625496B1

United States Patent
Ollivier (12) United States Patent
(10) Patent No.: US 6,625,496 B1
(45) Date of Patent: Sep. 23, 2003

(54) KIT AND METHOD FOR INSTALLATION OF A PROBE IMPLANTABLE IN THE CORONARY NETWORK FOR STIMULATION OF A CARDIAC CAVITY

(75) Inventor: Jean-Francois Ollivier, Villiers-le-Bade (FR)

(73) Assignee: ELA Medical S.A., Montrouge (FR)

( * ) Notice: Subject to any disclaimer, the term of this patent is extended or adjusted under 35 U.S.C. 154(b) by 0 days.

(21) Appl. No.: 09/854,542

(22) Filed: May 14, 2001

(30) Foreign Application Priority Data

May 16, 2000 (FR) ............................................. 00 06248
Oct. 10, 2000 (FR) ............................................. 00 12901

(51) Int. Cl.$^7$ ................................................. A61N 1/00
(52) U.S. Cl. ..................................................... 607/122
(58) Field of Search ........................ 607/115, 122–131, 607/37

(56) References Cited

U.S. PATENT DOCUMENTS

| | | | |
|---|---|---|---|
| 4,345,606 A | 8/1982 | Littleford | 128/784 |
| 5,246,014 A | * 9/1993 | Williams et al. | 607/122 |
| 5,322,509 A | 6/1994 | Rickerd | 604/53 |
| 5,423,772 A | 6/1995 | Lurie et al. | 604/282 |
| 5,476,498 A | 12/1995 | Ayers | 607/122 |
| 5,683,445 A | 11/1997 | Swoyer | 607/125 |
| 5,902,331 A | * 5/1999 | Bonner et al. | 600/585 |
| 6,033,414 A | 3/2000 | Tockman et al. | 606/129 |
| 6,356,791 B1 | * 3/2002 | Westlund et al. | 607/115 |

FOREIGN PATENT DOCUMENTS

| | | | |
|---|---|---|---|
| EP | 0 601 338 A1 B1 | 6/1994 | A61N/1/05 |
| EP | 0 993 840 A1 | 4/2000 | A61N/1/05 |
| WO | WO 99/55412 | 11/1999 | A61N/1/05 |

* cited by examiner

Primary Examiner—George R. Evanisko
Assistant Examiner—Omar Khan
(74) Attorney, Agent, or Firm—Orrick Herrington & Sutcliffe LLP (57) ABSTRACT

A method and kit for the installation of a probe, implantable in the coronary sinus network for stimulation of a cardiac cavity. The kit includes: a) a guiding catheter (14), having an internal lumen open at its two extremities and able to receive the probe (10) along its length; and b) an extension (22) comprising at its distal extremity a connector (24) engaging a monodiameter connector (20) at the proximal extremity of the probe (10). The external diameter of the connector (24) is the external diameter of the remainder of the extension (22). The external surface of the extension (22) is a surface having a low coefficient of friction as compared to the interior surface of the lumen of the guiding-catheter (14), and the external diameter is smaller than the interior diameter of the lumen of the guiding-catheter, so as to allow the guiding catheter to slide over and along the entire length of the extension, without a concomitant axial displacement of the probe. Preferably, the guiding catheter has a sufficient rigidity in torsion to allow the transmission of a rotational movement imparted at one extremity to the other extremity, and also has an increased flexibility in the vicinity of its distal extremity.

17 Claims, 5 Drawing Sheets

FIG_1

FIG_6

FIG_7

FIG_8

FIG_9

FIG_10

FIG_11

FIG_12

FIG_13

FIG_14

KIT AND METHOD FOR INSTALLATION OF A PROBE IMPLANTABLE IN THE CORONARY NETWORK FOR STIMULATION OF A CARDIAC CAVITY

FIELD OF THE INVENTION

The present invention relates to the installation of cardiac stimulation probes intended to be implanted in the coronary network of the heart to allow the stimulation of a left heart cavity by an "active implantable medical device", as such devices are defined by the Jun. 20, 1990 directive 90/385/CEE of the Council of the European Communities, and particularly a device such as a pacemaker, a defibrillator and/or a cardiovertor, and more particularly a pacemaker of the "multisite" type.

BACKGROUND OF THE INVENTION

The publication EP-A-0 993 840 and its corresponding U.S. patent application Ser. No. 09/416,140, which are commonly owned by the Assignee hereof, Ela Medical, describes a probe to be implanted in the coronary sinus network that is designed according to a number of precise criteria, in particular, criteria relating to the geometry and the flexibility of the distal part of the probe. U.S. application Ser. No. 09/416,140 is hereby incorporated herein by reference for the entirety of its disclosure.

Such a probe is not an endocavitary probe (such as are the probes for stimulating right heart cavities), but rather a probe to be introduced into the coronary network, to present an electrode disposed facing the left ventricle. Similarly, stimulation of the left atrium can be obtained by the choice of a different suitable stimulation site.

The access to the entry of the coronary sinus network is via the right atrium. The introduction of a probe through an endocavitary path is, however, a particularly delicate intervention. This is due to the fact that the position of the stimulation point (i.e., where the electrode contacts the tissue) is very important in the case of a "multisite" type pacemaker, where the left ventricle and right ventricle stimulation sites have to be spaced as far apart as possible to optimize the resynchronization of all of the cardiac cavities.

One of the techniques known for installing such a probe uses an accessory called a "guiding catheter" as described, for example, in the PCT publication WO-A99/55412. A guiding catheter is typically a hollow tube or sheath reinforced by a wire mesh, having an interior lumen with a surface that has a low coefficient of friction (for example, a surface of PTFE co-extruded or co-molded with the remainder of the sheath). The tube also has a flexibility that is selected so as to have a sufficient rigidity in torsion, to allow the transmission of a rotational movement imparted at one end to the other end, in order to be able to adjust the orientation of the extremity of the probe against the myocardium during installation of the probe.

In addition, the guiding catheter is typically of the "soft tip" type, i e in its terminal region, its flexibility increases as one approaches the distal end. This variation in flexibility is provided to allow an atraumatic approach of the guiding catheter in the coronary network and to cross obstacles such as valvules without too many difficulties and without wounding tissue.

Once installed in place, the guiding catheter constitutes a direct "tunnel" between the "external world" and the coronary sinus, that the surgeon can then use to slide the probe through until the probe reaches the final position. At this stage, an important difficulty arises with respect to the withdrawal of the guiding catheter. The guiding catheter withdrawal must of course be operated without dislodging or modifying the orientation of the installed probe.

Until now, at the time of its withdrawal, the guiding catheter has typically been cut at its proximal end near the generator by means of a cutting tool, located on the terminal extremity. The cutting tool is used to split both the end-handle of the guiding catheter and the wire mesh forming the reinforcement of the hollow tube. This technique of cutting the sheath away from the guiding catheter after installation of the probe presents a risk of damaging the probe because of the proximity of the cutting tool to the body of the probe, i.e., short distance of about 1 mm.

Installation kits of a different structure have been proposed to cure this disadvantage, with, for example, a sheath that is peelable, but not reinforced. Unfortunately, the pre-cutting of the sheath along its length to make it peelable also results in a weakness and a lesser rigidity of the tube, with a risk of the tube folding or collapsing, and a less effective transmission of the effort exerted at the proximal end at the time of the implantation.

Thus, there is a continuing need for a satisfactory solution to the problem of withdrawal of the guiding catheter, a process which still remains extremely dependent on the dexterity of the surgeon and the usual risks of a complex intervention of this nature.

OBJECTS AND SUMMARY OF THE INVENTION

It is, therefore, an object of the present invention to propose an installation kit for a coronary sinus probe that mitigates the above-mentioned difficulties by allowing an easy and sure withdrawal of the guiding catheter, yet is freed from a dependency on the degree of dexterity of the operator.

Broadly, the installation kit of the present invention includes a guiding catheter and an extension. The guiding catheter is of a type in itself known, i.e., comprising an internal lumen open at its two ends and able to receive the probe along its length. The guiding catheter also is preferably provided with a sufficient torsional rigidity to allow the transmission of a rotational movement imparted at one extremity to the other extremity, and it also has a so-called soft tip, that is an increased flexibility in the vicinity of its distal extremity.

The extension comprises a member having a proximal extremity, a distal extremity, an internal lumen open at its two ends, and a connector element at its distal extremity that mounts to the proximal extremity of the probe. The probe proximal extremity is provided with a length having a uniform diameter ("monodiameter"). The extension connector has an external diameter that is substantially the same as the diameter of the remainder of the extension. The extension has an external surface that has a low coefficient of friction as compared to the interior surface of the lumen of the guiding catheter. The external diameter of the extension is smaller than the interior diameter of the lumen of the guiding catheter, so as to allow an axial slip of the guiding catheter along the entire length of the extension (including the extension connector), without a concomitant axial displacement of the probe.

Advantageously, in preferred embodiments, the present invention is variously directed to an installation kit also including one or more of the following elements:

(1) a long stylet, able to be inserted in an internal lumen of the extension at a proximal extremity, the length of the long stylet being greater than the sum of the lengths of the probe and the extension;

(2) a sleeve, able to be fitted on the monodiameter proximal extremity of the probe, so as to form an electric connection plug connectable to a connector head of a pacemaker or defibrillator, preferably in conformity with the system connection standard IS-1;

(3) a short stylet, able to be inserted jointly in the sleeve and an internal lumen of the probe at the proximal extremity of the probe; and (4) a tool comprising a distal housing able to receive the short stylet and also be threaded on the monodiameter proximal extremity of the probe; this tool more preferably also including a depth gauge for use in adjusting the axial penetration depth of the sleeve relative to the monodiameter proximal extremity of the probe.

The invention also is directed to a method of installing a coronary sinus probe using the kit(s) described herein.

BRIEF DESCRIPTION OF THE DRAWINGS

Further features, advantages and characteristics will become apparent to a person of ordinary skill in the art in view of the following detailed description, made with reference to the annexed drawings, in which like reference characters refer to like elements, and in which.

DETAILED DESCRIPTION OF THE DRAWINGS

One now will describe the protocol of a kit for installing probes according to the present invention, as well as the various accessories that may constitute the kit, with reference to FIGS. 1 to 9. In the drawings, reference 10 indicates a coronary sinus probe, for example, a probe of a type comparable with that described in the publication EP-A-0 993 840 and the corresponding U.S. application Ser. No. 09/416,140 mentioned above.

Probe 10 is associated with a stylet 12 made of a relatively rigid material. One can make stylet 12 penetrate the body of probe of (ie., a lumen in said probe) to a greater or lesser depth. One also can deform stylet 12 to allow a better general orientation of the distal extremity of the probe at the time of the installation. Reference is made to the published EP-A-0993 840 and corresponding U.S. patent application Ser. No. 09/416,140 for more details concerning the potential role of this stylet 12 in inserting probe 10.

Probe 10 equipped with stylet 12 thus will be introduced into the internal lumen or channel of a guiding catheter 14, of a type in itself known, for example, comparable with that described in the above mentioned WO-A-99/55412. The guiding catheter 14 is advantageously provided at its proximal extremity with a handle 16 for handling as well as haemostatic valve (not represented, but well known to a person of ordinary skill in the art), although the handle and valve form no part of the present invention.

To install the guiding catheter 14 in the coronary network, the surgeon starts by placing a conventional percutaneous introducer of suitable size (at least 9 French in size) at the selected access point in a manner known to persons of ordinary skill in the art. The surgeon then removes the introducer while leaving in place there the spiral guide (not shown). The surgeon then introduces an assembly including the haemostatic valve, the guiding catheter, a dilating catheter in the introducer and on the spiral guide, all in accordance with the known installation procedures of such a guiding catheter.

Once it has arrived in the right atrium, the guiding catheter is retracted (ie., is withdrawn) a few centimeters from the dilating catheter in order to let the atraumatic (non-traumatic or a soft tip) extremity of the guiding catheter appear.

Then, under amplifier of brightness (e.g., a fluoroscope), this extremity penetrates the coronary sinus ostium. This procedure can be facilitated by use of an electrophysiology probe placed in the guiding-catheter in a known manner.

Once the guiding catheter is installed, the surgeon withdraws any guide wire or another apparatus that was used for the placement of the guiding-catheter, closes the haehostatic valve and purges the guiding catheter using the lateral output of the haemostatic valve.

The surgeon can then carry out the placement of the probe in the guiding catheter thus installed. This step corresponds to what is illustrated schematically on FIG. 1(*a*)). In this regard, the probe 10 is taken out of its box, the surface of the probe body is humidified with a physiological salt solution, and stylet 12 is threaded in the internal channel of the probe. The guiding catheter is again purged using the lateral output of the haemostatic valve. The valve is then opened and the probe 10, rigidified by the straight stylet 12 is introduced into the guiding catheter 14. The haemostatic valve having been adjusted to the diameter of the body of the probe, the final placement of the probe 10 in the coronary network is then carried out. The resulting configuration is that illustrated in FIG. 1(*b*). Lastly, the guiding catheter 14 remaining in place, the surgeon withdraws stylet 12 from probe 10. This configuration corresponds to FIGS. 1(*c*) and 2.

The surgeon carries then out the withdrawal of the guiding catheter 14, in accordance with the manner taught by the present invention. The first step of the withdrawal is extending the proximal extremity 20 of the probe, which emerges from the guiding-catheter 14, by coupling an extension 22 to the proximal extremity 20 in accordance with the present invention.

The proximal extremity 20 of the probe 10 has a monodiameter connector (ie., the diameter of this connector is relatively uniform along a distance, which diameter is not greater than the diameter of the probe body) intended to be subsequently inserted in the connection head of a pacemaker to ensure the electric connection between the pulse generator (not shown) and the stimulation electrode (not shown) located at the other extremity (the distal extremity) of the probe 10. The probe is preferably covered on its exterior by a material having a low coefficient of friction (low as compared to the lumen interior surface of the guiding-catheter 14), except for the extremities. The material may be, for example, a coating of a hydrogel made primarily (about 99%) of polyvinylpyrrolidone, with approximately 1% of an adhesive agent to adhere the layer of polyvinylpyrrolidone to the silicone of the tube.

The extension 22 is preferably construed in the form of a monodiameter tube, for example, a polyurethane tube. The length of the extension 22 is slightly greater than that of the guiding catheter 14; its diameter is smaller than the interior diameter of the lumen of the guiding catheter 14. The extension 22 also has a good mechanical resistance (i.e., a certain stiffness which ensures a proper support when it is held only by the one of its extremities) and requiring only a weak insertion effort for its connection (typically a frictional fit) to the monodiameter connector 20. The extension is, for example, equipped with a female housing 24 (shown in FIG. 3) forming a casing, homologous with the monodiameter connector 20 of probe 10. Extension 22 also may be split along a part of its length to allow an adjustment of the fit to connector 20 when these two elements were plugged together, e.g., with one fitting over the other.

Figure 1:
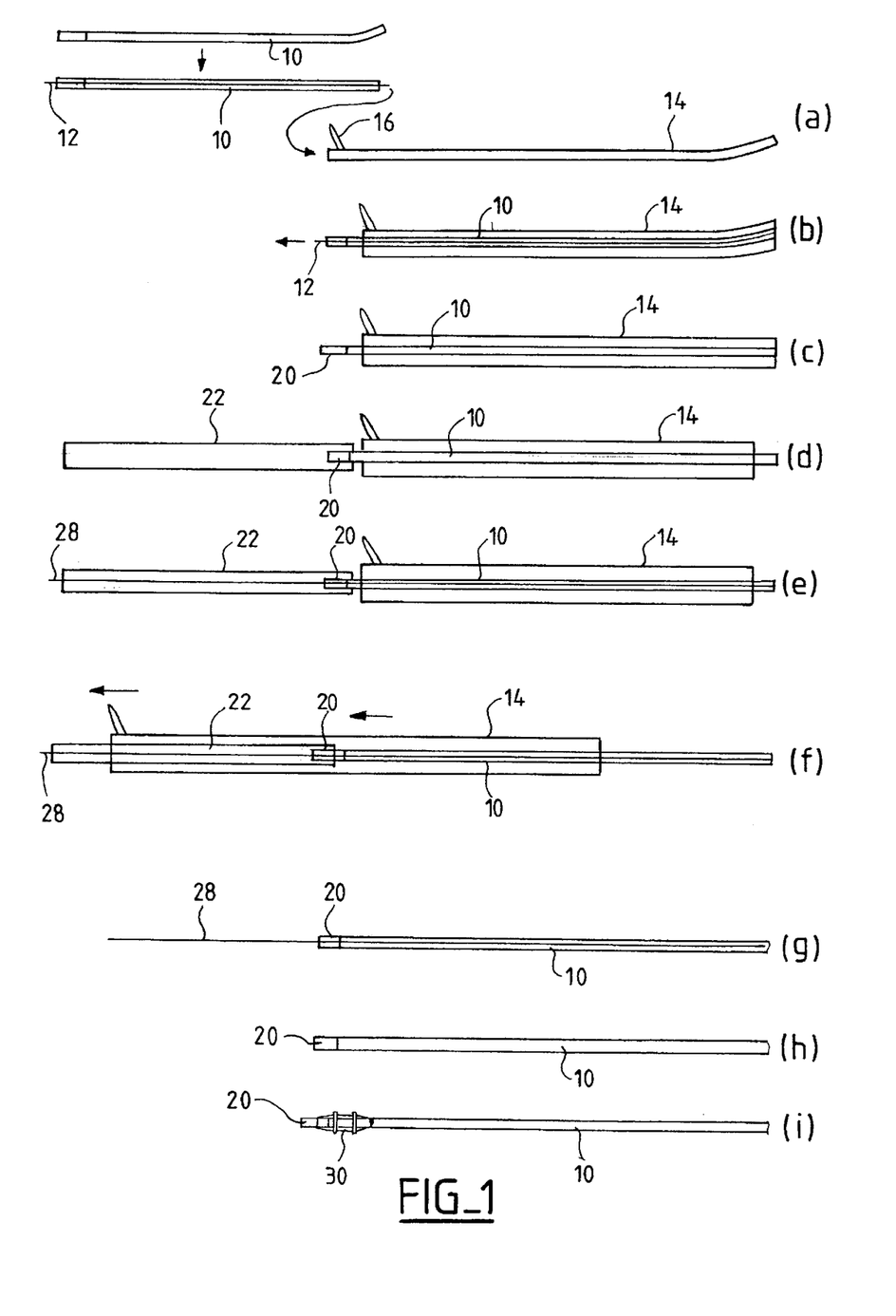
FIG. 1 schematically illustrates the various steps (a) to (i) of installation of a coronary probe using a kit in accordance with a preferred embodiment of the present invention.
Figures 2, 3, 4, 5:
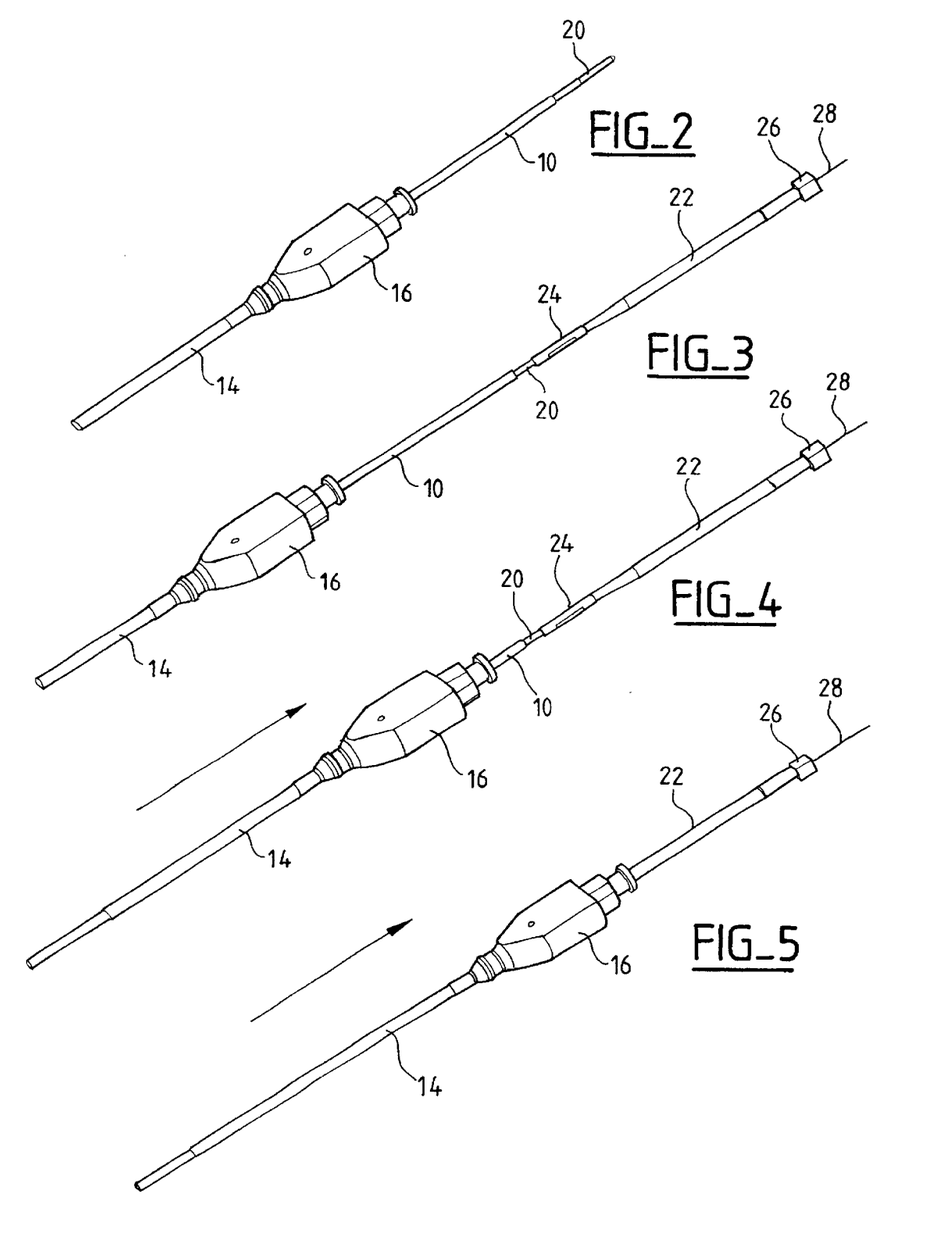
FIGS. 2 to 9 are elevated perspective views showing in more detail the steps of FIG. 1.

Once extension 22 is mounted, the configuration is that illustrated in FIG. 1(d). The surgeon then inserts a stylet 28 through the proximal extremity 26 (FIG. 3) of extension 22. Stylet 28 is a long stylet that has a length that is greater than the sum of the lengths of probe 10 and extension 22. Stylet 28 makes it possible to maintain probe 10 in position and avoids its possible dislodgment at the time of the following steps; it is desirable to insert the stylet 28 until it extends beyond the coronary sinus for at least a few centimeters, until even with the extremity of the probe. The configuration of the assembly is then that illustrated FIGS. 1(e) and 3.

The following step, preferably performed under the amplifier of brightness, is to slide the guiding catheter 14 along probe 10 (a first intermediate position is illustrated in FIG. 4), then along the extension 22 (a second intermediate position is illustrated in FIGS. 1(f) and 5), maintaining the probe 10 and extension 22 as stationary as possible, until the guiding catheter 14 is completely disengaged from the probe 10.

Figures 6, 7:
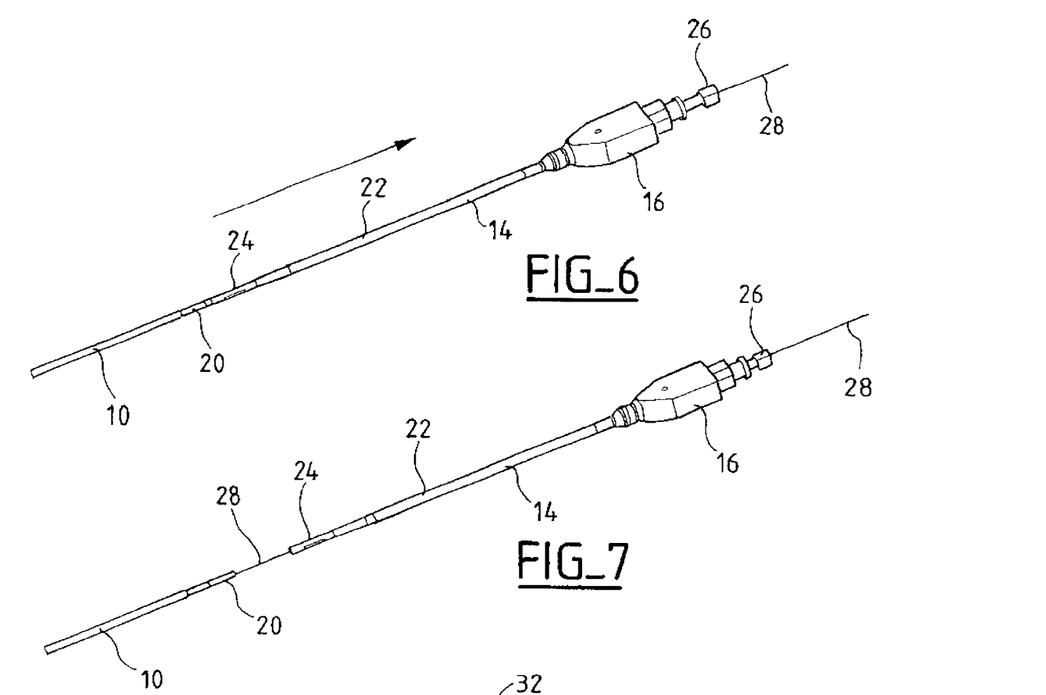

FIGS. 6 and 7 illustrate other intermediate positions of the withdrawal process.

The surgeon then disconnects the extension 22 from probe 10 resulting in the configuration illustrated in FIG. 1(g) and, under the amplifier of brightness, withdraws the stylet 28 (resulting in the configuration illustrated in FIG. 1(h)).

The next step is a step of completing the connector. Indeed, the proximal extremity of the probe 10 being a simple monodiameter connector 20, it is necessary to adapt thereto a sleeve 30 to transform the monodiameter connector 20 into a connection plug that conforms in particular to the standardized connection system of IS-1 of coronary probe connectors. This leads to the configuration of FIG. 1(i), where probe 10 is able to be connected to a pacemaker or defibrillator by the electric connection plug made of the connector monodiameter 20 and sleeve 30 mounted thereon.

In this respect, one can refer to the French and European standard NF EN 50077"Connector with low profile for implantable pacemaker", which defines the standardized connection system known as "IS-1." This standard provides for the interchangeability of the probes and the pulse generators produced by various manufacturers. It should be understood however, that the invention is not limited to the particular case of connection systems according to this standard, nor even with the connection systems for a pacemaker. Preferably, however, the case of the device includes a body containing the various electronic circuits and the battery, and a connector head mechanically and electrically connected to the body. The connector head is equipped with one or more cavities suitable to receive the probes, and screws to hold the probe connectors in place.

Figure 8:
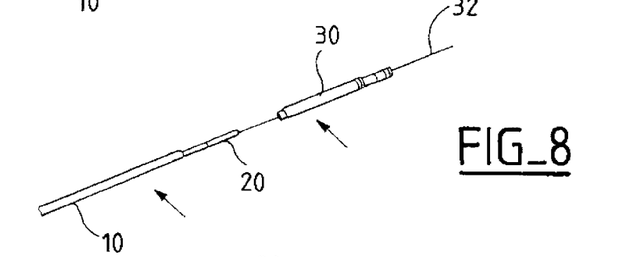
Figure 9:
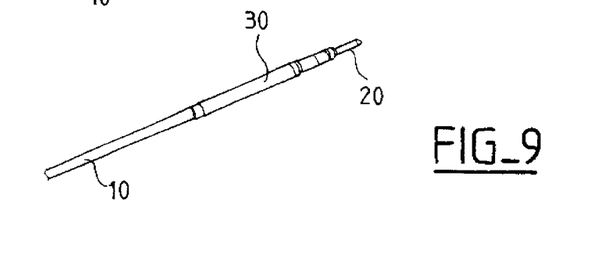

After having cleaned the monodiameter connector 20 and having soaked the extremity of sleeve 30 in a lubricant, e.g., dipping it in a flask of mineral oil, the surgeon threads a stylet 32 into sleeve 30 as illustrated in FIG. 8. Stylet 32 is a relatively short stylet. The surgeon then soaks the extremity of the monodiameter connector 20 in the mineral oil, and thereafter inserts stylet 32 in the internal lumen of the probe to rigidify the latter over a length of about 10 to 15 cm. He finally slides sleeve 30 on over the connector monodiameter 20 until it comes to a stop against a flange or block (one example being described below with reference to FIG. 10). Stylet 32 is then withdrawn and any surplus oil is wiped off. The final configuration obtained is that illustrated in FIG. 9. The connection plug thus carried out can then, after lubrication, be inserted into the connector head of the pacemaker, where it will be finally maintained in place by tightening the screws that are typically provided in the connector head.

Figure 10:
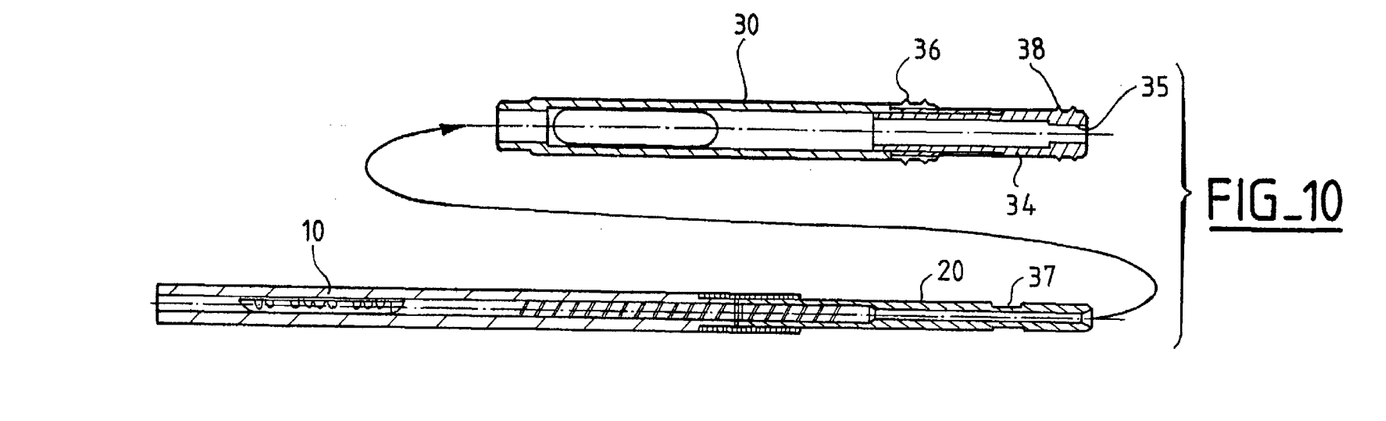
FIG. 10 shows the proximal extremity of the probe and the sleeve on the extremity of the probe, before installation.

FIG. 10 shows in cross section, the monodiameter connector 20 of probe 10 and sleeve 30. The interior diameter of part 34 of sleeve 30 receiving the extremity of the probe 10 corresponds to that of the monodiameter connector 20. An area 35 having a smaller diameter at the proximal extremity of sleeve 30 cooperates with a bottle-neck or detent section 37 in connector 20, so as to produce an effect of click-and-ratchet during the assembly of these two elements, and thereafter to prevent any undesired mutual longitudinal displacement of these two elements, in order to respect the dimensions of the IS-1 standard.

Figure 11:
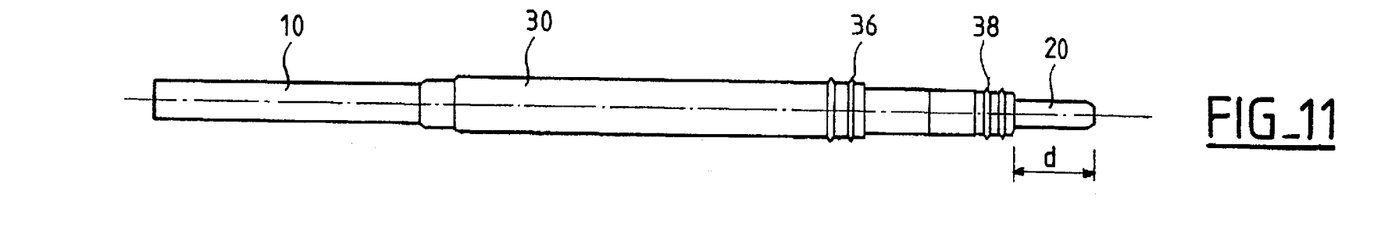
FIGS. 11 and 12 show, in elevated and cross section views respectively, the proximal extremity of the probe equipped with a sleeve.
Figure 12:
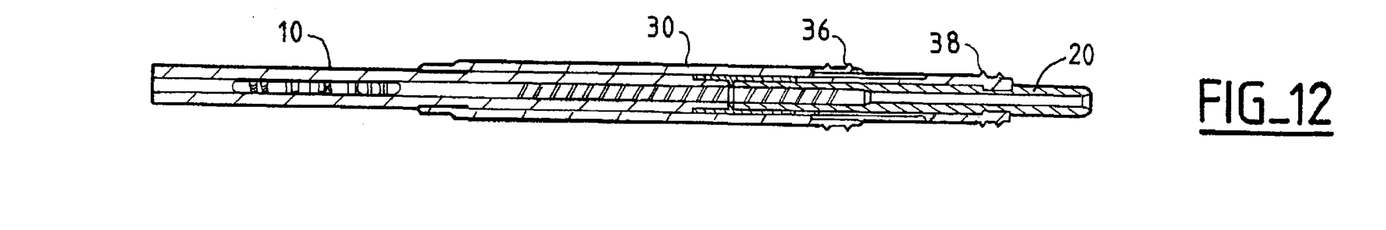

FIGS. 11 and 12 show the plug obtained after placement of the sleeve 30 on the connector 20 of probe 10, respectively in elevated and cross section views.

As one skilled in the art will understand, the free lead portion of the monodiameter connector 20 extends beyond the part 34 in which it was encased, and it is this emerging part that makes the electric connection with the connector head of the pacemaker case.

Sleeve 30 preferably carries peripheral reliefs 36, 38 (only two sets of two are illustrated, but more or less may be employed depending on the manufacturing tolerances and standard used), making it possible to obtain a seal between the plug and the housing of the connector receiving this element, in conformity with above-mentioned standard IS-1.

Figure 13:
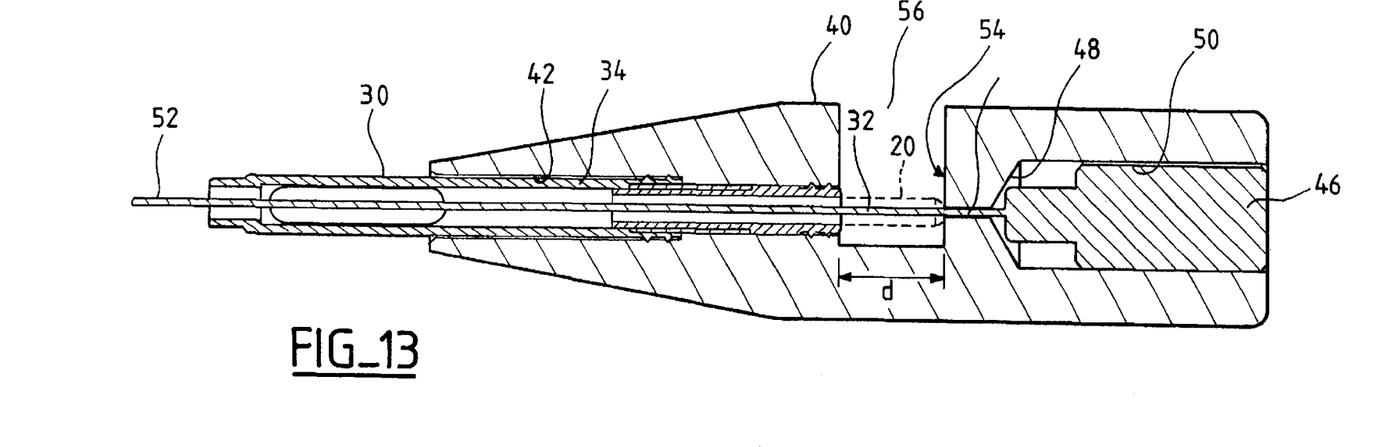
FIGS. 13 and 14 show, in cross section and perspective views respectively, a tool for installing the sleeve on the proximal extremity of the probe.
Figure 14:
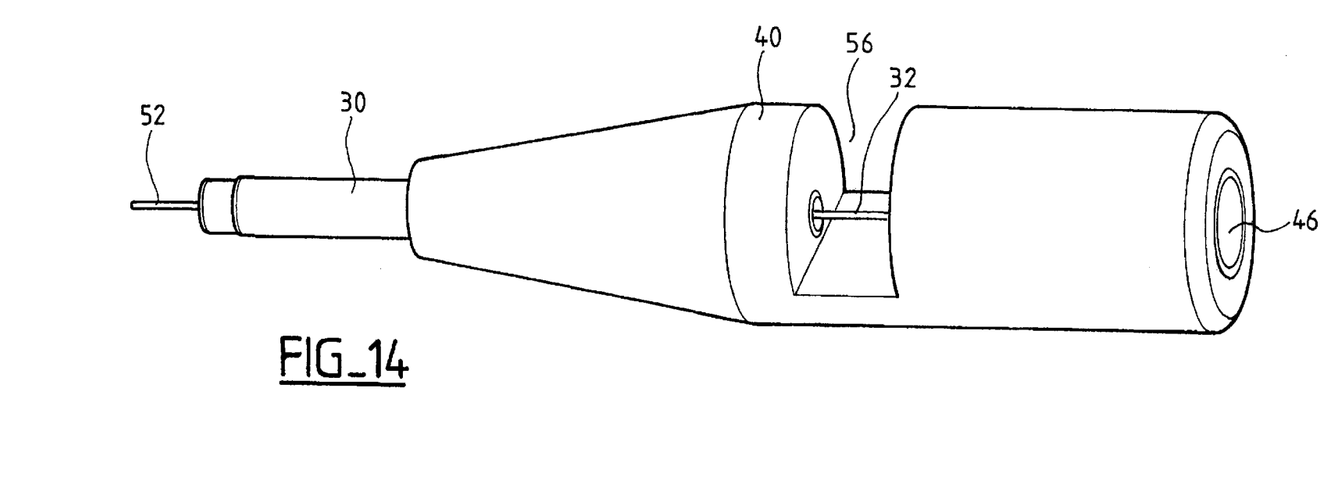

The placement of the sleeve 30 on the monodiameter connector 20 of probe 10 also can advantageously be carried out by means of an ad hoc tool 40, such as that illustrated in FIGS. 13 and 14. Tool 40 comprises a distal housing 42 able to receive part 34 of sleeve 30 and surrounding the monodiameter connector 20. Very advantageously, tool 40 is provided with sleeve 30 already installed, as constructed at the factory for a direct use by the surgeon as it is removed from the sterile/aseptic packaging.

Tool 40 comprises at its proximal portion an opening 44 in which can be inserted stylet 32 after installation of sleeve 30. In the case that tool 40 is pre-loaded with sleeve 30, stylet 32 also may be set in tool 40 at the factory.

On the proximal side, stylet 32 is finished with a handle 46 which is constructed so that when the stylet is inserted for the desired length, it comes to rest (in blockage) against a bottom or stop 48 of proximal cavity 50 in tool 40.

In this position, stylet 32 entirely passes through sleeve 30 and emerges on the distal side 52, over a length on the order of ten centimeters. The monodiameter connector 20 of the probe 10 is then threaded on the emerging part 52 of the stylet, and it comes to penetrate gradually with interior of sleeve 30 over its entire length, then beyond, so that the extremity of the monodiameter connector 20 emerges in the position represented in dotted lines on FIG. 13, until coming to rest against a wall 54 in cavity 56 formed in a central portion of tool 40.

Tool 40 is used thus as a depth gauge to allow the placement of the sleeve 30 over the monodiameter connector 20 along a length, making it possible to very precisely adjust dimension d (shown in FIGS. 11 and 13) of the emerging part of connector 20. Tool 40 and stylet 32 are then easily withdrawn by traction, once sleeve 30 is installed.

One skilled in the art will appreciate that the present invention can be practiced by embodiments other than those disclosed herein, which embodiments are presented for purposes of illustration and not of limitation.

I claim:

1. A kit for installing a probe implantable in the coronary network for stimulation of a cardiac cavity, said kit comprising:
   a) a probe comprising a length, a proximal extremity, and a monodiameter connector at said proximal extremity;
   b) a guiding catheter comprising an internal lumen, said internal lumen having an interior diameter, an interior surface having a coefficient of friction, a first open extremity and a second open extremity and a length dimension, and
   c) an extension having a proximal extremity and a distal extremity, an internal lumen, an external diameter that is less than the interior diameter of the lumen of the guiding catheter, an external surface comprising a coefficient of friction that is lower than the coefficient of friction of the interior surface of the lumen of the guiding catheter, and a connector at the distal extremity to connect the extension distal extremity to the monodiameter connector of the probe without insertion into the monodiameter connector of the probe, the monodiameter connector having an external diameter that is substantially the same as the external diameter of the extension, wherein the guiding catheter is slideable along the entire length of the extension without a concomitant axial displacement of the probe connected to said extension.

2. The kit of claim 1, further comprising a stylet having a length and a proximal extremity, said stylet able to be inserted in the internal lumen of the extension, the stylet length being greater than a sum of the lengths of the probe to be installed and the extension.

3. The kit of claim 1, further comprising a sleeve able to be encased on the monodiameter connector of the probe to form a plug for electric connection to a connector head of a pacemaker or a defibrillator.

4. The kit of claim 3, wherein said probe further comprises an internal lumen having a proximal extremity, and wherein said kit further comprises a stylet having a length sufficient to be inserted in said sleeve and said proximal extremity of said internal lumen of said probe.

5. The kit of claim 4, further comprising a tool for placement of the sleeve, said tool comprising a distal housing able to receive said stylet, and said stylet able to be threaded on the proximal extremity of the probe monodiameter connector.

6. The kit of claim 5, wherein said tool further comprises a depth gauge able to adjust a depth (d) of axial penetration of the sleeve on the proximal extremity of the probe monodiameter connector.

7. The kit of claim 3, wherein said sleeve further comprises a set of dimensions in conformity with the connection system standard IS-1.

8. The kit of claim 1, further comprising:
   c) a stylet having a length and a proximal extremity, able to be inserted in the internal lumen of the extension, the stylet length being greater than a sum of the lengths of the probe and the extension.

9. The kit of claim 8 further comprising a sleeve able to be encased on the monodiameter connector of the probe to form a plug for electric connection to a connector head of a pacemaker or a defibrillator.

10. A method for installing a probe implantable in the coronary network for stimulation of a cardiac cavity, said method comprising:
    a) providing a probe having a length, a proximal extremity, and a monodiameter connector at said proximal extremity;
    b) providing a guiding catheter having an internal lumen, said internal lumen including an interior diameter, an interior surface and a coefficient of friction, a first open extremity and a second open extremity and a first length;
    c) providing an extension having a proximal extremity and a distal extremity, an internal lumen, an external diameter that is less than the interior diameter of the lumen of the guiding catheter, an external surface comprising a coefficient of friction that is lower than the coefficient of friction of the interior surface of the lumen of the guiding-catheter, and a connector at the distal extremity to connect the extension distal extremity to the monodiameter connector of the probe without insertion into the monodiameter connector of the probe, the connector having an external diameter that is substantially the same as the external diameter of the extension, wherein the guiding catheter is slideable along the entire length of the extension without a concomitant axial displacement of the probe connected to said extension;
    d) inserting the guiding catheter in the coronary sinus network;
    e) inserting the probe in the guiding catheter to install said probe in said coronary sinus network;
    f) connecting the extension to the proximal end of the probe;
    g) removing the guiding catheter from said patient while maintaining the probe in its installed position; and
    h) disconnecting the extension from said probe.

11. The method of claim 10, further comprising providing a sleeve able to be encased on the monodiameter connector of the probe to form a plug for electric connection to a connector head of pacemaker or defibrillator, the method further comprising:
    i) installing the sleeve on said monodiameter connector.

12. The method of claim 11, further comprising providing a stylet having a length sufficient to be inserted in said sleeve and the proximal extremity of said probe internal lumen, and wherein step i) further comprises installing said stylet in said sleeve and in said monodiameter connector.

13. The method of claim 12, further comprising providing a tool for placement of the sleeve, said tool comprising a distal housing able to receive said stylet, and said stylet able to be threaded on the proximal extremity of the probe monodiameter connector.

14. The method of claim 10, further comprising providing a stylet having a length greater than a sum of the lengths of the probe to be installed and the extension, and, after step f) and before step g), the method further comprises inserting the stylet in the internal lumen of the to extension and the probe.

15. A kit for installing a probe implantable in the coronary network for stimulation of a cardiac cavity said kit comprising:
   a) a probe comprising a length, a proximal extremity, a monodiameter connector at said proximal extremity, and an internal lumen having a proximal extremity;
   b) a guiding catheter comprising an internal lumen, said internal lumen having an interior diameter, an interior surface having a coefficient of friction, a first open extremity and a second open extremity and a length dimension, and
   c) an extension having a proximal extremity and a distal extremity, an internal lumen, an external diameter that is less than the interior diameter of the lumen of the guiding catheter, an external surface comprising a coefficient of friction that is lower than the coefficient of friction of the interior diameter of the lumen of the guiding catheter, and a connector at the distal extremity to connect the extension distal extremity to the monodiameter connector of the probe, the monodiameter connector having an external diameter that is substantially the same as the external diameter of the extension, wherein the guiding catheter is slideable along the entire length of the extension without a concomitant axial displacement of the probe connected to said extension;
   d) a sleeve able to be encased on the monodiameter connector of the probe to form a plug for electric connection to a connector head of a pacemaker or a defibrillator;
   e) a stylet having a length sufficient to be inserted in said sleeve and said proximal extremity of said internal lumen of said probe; and
   e) a tool for placement of the sleeve, said tool comprising a distal housing able to receive said stylet and said stylet able to be threaded on the proximal extremity of the probe monodiameter connector.

16. The kit of claim 15, wherein said tool further comprises a depth gauge able to adjust a depth (d) of axial penetration of the sleeve on the proximal extremity of the probe monodiameter connector.

17. A method for installing a probe implantable in the coronary network for stimulation of a cardiac cavity, said method comprising:
   a) providing a probe having a length, a proximal extremity, and a monodiameter connector at said proximal extremity;
   b) providing a guiding catheter having an internal lumen, said internal lumen including an interior diameter, and interior surface and a coefficient of friction, a first open extremity and a second open extremity and a first length;
   c) providing an extension having a proximal extremity and a distal extremity, an internal lumen, an external diameter that is less than the interior diameter of the lumen of the guiding catheter, an external surface comprising a coefficient of friction that is lower than the coefficient of friction of the interior surface of the lumen of the guiding catheter, and a connector at the distal extremity to connect the extension distal extremity to the monodiameter connector of the probe, the connector having an external diameter that is substantially the same as the external diameter of the extension, wherein the guiding catheter is slideable along the entire length of the extension without a concomitant axial displacement of the probe connected to said extension;
   d) inserting the guiding catheter in the coronary sinus network;
   e) inserting the probe in the guiding catheter to install said probe in said coronary sinus network;
   f) connecting the extension to the proximal end of the probe;
   g) removing the guiding catheter from said patient while maintaining the probe in its installed position;
   h) disconnecting the extension from said probe;
   i) providing a sleeve able to be encased on the monodiameter connector of the probe to form a plug for electric connection to a connector head of pacemaker or defibrillator;
   j) installing the sleeve on said monodiameter connector;
   k) providing a stylet having a length sufficient to be inserted in said sleeve and the proximal extremity of said probe internal lumen;
   l) installing said stylet in said sleeve and in said monodiameter connector; and
   m) providing a tool for placement of the sleeve, said tool comprising a distal housing able to receive said stylet, and said stylet able to be threaded on the proximal extremity of the probe monodiameter connector.

* * * * *

UNITED STATES PATENT AND TRADEMARK OFFICE
CERTIFICATE OF CORRECTION

PATENT NO. : 6,625,496 B1
DATED : September 23, 2003
INVENTOR(S) : Ollivier

It is certified that error appears in the above-identified patent and that said Letters Patent is hereby corrected as shown below:

Column 4,
Line 26, delete "haehostatic" and insert -- haemostatic -- therefor;
Line 45, delete "carries then" and insert -- then carries -- therefor;

Column 5,
Line 8, delete "by the one" and insert -- by one -- therefor;
Line 27, delete "illustrated" and insert -- illustrated in -- therefor; and Column 8,
Line 2, delete "c)" and insert -- d) -- therefore.

Signed and Sealed this

Third Day of May, 2005

JON W. DUDAS
*Director of the United States Patent and Trademark Office*